| United States Patent [19] | [11] Patent Number: 4,931,431 |
| --- | --- |
| Livingston | [45] Date of Patent: * Jun. 5, 1990 |

[54] ARTHRITIS TREATMENT WITH HYPOXANTHINE

[76] Inventor: William S. Livingston, 1080 Triunfo Canyon Rd., West Lake Village, Calif. 91361

[*] Notice: The portion of the term of this patent subsequent to Aug. 1, 2006 has been disclaimed.

[21] Appl. No.: 201,641

[22] Filed: Jun. 2, 1988

Related U.S. Application Data

[63] Continuation-in-part of Ser. No. 907,623, Sep. 15, 1986.

[51] Int. Cl.$^5$ .................. A61K 31/52; C07H 19/16
[52] U.S. Cl. .................. 514/46; 536/24; 536/26
[58] Field of Search .................. 514/46, 262; 536/24, 536/26; 544/265

[56] References Cited

U.S. PATENT DOCUMENTS

| | | | |
| --- | --- | --- | --- |
| 3,526,697 | 9/1970 | Livingston | 424/105 |
| 4,081,534 | 3/1978 | Elion et al. | 424/180 |
| 4,309,419 | 1/1982 | Wolberg et al. | 424/180 |
| 4,322,411 | 3/1982 | Vinegar et al. | 424/180 |

OTHER PUBLICATIONS

Carson et al., *Proc. Natl. Acad. Sci.* (U.S.A.), 79(12), 3848–52, (1982).
Glazer, Robert I., *Cancer Chemotherapy, Pharmacol.*, 4, 227–235 (1980).
Ratech, Howard et al., (1982), *Cellular Immunology*, 244–251.

*Primary Examiner*—John W. Rollins
*Assistant Examiner*—Gary L. Kunz
*Attorney, Agent, or Firm*—Hale and Dorr

[57] ABSTRACT

The complex mixture of substances in the product made from human placentae according to the procedure described in U.S. Pat. Nos. 3,526,697 and 4,335,040 includes hypoxanthine. Hypoxanthine is effective in treating arthritis, particularly if administered intradermally at low (e.g., not more than about 0.1 mg. of hypoxanthine per does) dose. Preferably, the dose level is not more than about 0.00002 mg. active material per dose, e.g., 0.1 cc of a dilution not stronger than about 1 mg. of active material per 5,000 ml of diluent.

3 Claims, No Drawings

ARTHRITIS TREATMENT WITH HYPOXANTHINE

This application is a continuation-in-part of U.S. Ser. No. 06/907,623 filed Sept. 15, 1986.

FIELD OF THE INVENTION

This invention relates to the treatment of arthritis and more particularly, to such treatment by intradermal administration of low doses of hypoxanthine.

BACKGROUND OF THE INVENTION

U.S. Pat. Nos. 3,526,697 and 4,335,040 disclose producing a therapeutic product by a process of autolysis of animal tissue in which a quantity of material comprising animal tissue is placed in a pressure vessel, the vessel is enclosed, sealed, and maintained at a temperature in the range of about 5 to about 65 degrees centigrade and a pressure in the range of about 15 to 45 psig for a period of not less than about two weeks, and the liquid portion of the semi-liquid thereby produced is recovered and sterilized. As discussed in such patents, the material thus produced is useful in the treatment of rheumatoid arthritis and osteoarthritis. The patents state that treatment is by intravenous or intercutaneous injection, preferably intercutaneous, and that mice have been treated intraperitonically.

Livingston Placental Autolyste ("LPA") is a complex mixture of substances derived from the autolysis of human placentae under the conditions defined in the patents, and in the California veterinary industry is known as "Scott A-510". The use of LPA in the treatment of cancer tumors and arthritis has been reported in e.g., Livingston, W. S., "The Treatment of Spontaneous Tumors of the Dog and Cat With a Filtrate From a Tissue Lysate", J. Nat. Cancer Inst., 1958, 20:245-306; Livingston, W. S., "Growth Inhibition of Transplantable Mouse Lyphosarcoma by a Filtrate from Placental Lysate", J. Nat. Cancer Inst., 1959, 23:597-603; Bender, W. M. "Nontraditional Treatment of Mycosis Fungoides in a Dog", J. Am. Vet. Med. Assn. 1984, 185:900-901; and Maxson, T. R. and Compton, E. L., "Controlled Study of a New Anti-Arthritic Substance", Ann. Allergy, 1969, 21:54-64.

SUMMARY OF THE INVENTION

It has now been discovered that the complex mixture of substances in LPA, i.e., in products made from human placentae according to the procedure described in the aforementioned patents, includes hypoxanthine. Isolation of hypoxanthine as the active ingredient with respect to treating arthritis has been accomplished through a series of fractionations of LPA and administration of the fractions to arthritic dogs to determine activity with respect to reducing the arthritic condition.

In a first stage of the determination, the LPA was fractionated by membrane filtration which separated out compounds having an atomic weight of greater than 500 Daltons on the one hand and less than 500 Daltons on the other. (A suitable filtration series is provided by Amicon Co., Filters XM-50 through UM-05. Amicon has an address at 182 Conant Street, Danvers, Mass. 01923.) It was found, by clinical administration of the fractions, that the fraction of compounds weighing less than 500 Daltons contained the active ingredient. Next, this active fraction was fractionated using a Sephadex gel, which fraction, when analyzed by spectral analysis with respect to optical density was seen to separate into at least two identifiable, separable, fractions. Of the fractions, one was determined to contain the active ingredient and this fraction was further analyzed and refined using more sensitive gel technology, including larger stacks and high resolution recycling. By virtue of this additional refinement, it was ultimately determined that one fraction contained a single compound. This compound was identified using X-ray diffraction and mass spectroscopy to be hypoxanthine.

It has also been discovered that hypoxanthine is particularly effective in treating arthritis if administered intradermally at low (e.g., not more than about 0.01 mg., and preferably about 0.00002 mg., of hypoxanthine) dose.

A first aspect of the invention accordingly features the method of treating a human or other mammalian arthritic subject by intradermal administration of a low dose of hypoxanthine, and a second aspect features the method of such treatment which comprises the administration, intradermal or otherwise, of a low dose of hypoxanthine that has been produced other than by autolysis, i.e., by a method other than that disclosed in the aforementioned patents. In preferred practices, which encompass both aspects, the dose level is not more than about 0.00002 mg. active material (e.g., 0.1 cc dose of a dilution not stronger than about 1 mg. of active material per 5,000 cc of diluent,) the dose is injected intradermally

DETAILED DESCRIPTION OF A PREFERRED EMBODIMENT OF THE INVENTION

Sigma grade hypoxanthine, was obtained from Sigma Chemical Co. of St. Louis, Mo. Using this material, a number of tests were conducted.

In each test, the active material to be administered was dissolved in a normal physiological saline solution. Typically, 100 mg of hypoxanthine was dissolved in 1000 ml of saline, and is referred to below as a "normal preparation". This dilution was then further adjusted (e.g. a further dilution by 1:500) to insure that a 0.1 cc dose would include the desired quantity for the particular test (e.g. 0.00002 mg) of the active material. The resulting active material-saline dilution was injected intradermally, preferably just below the squamous layer.

Hypoxanthine has been found to be effective in treating arthritis, both rheumatoid and osteoarthritis. In treating both dogs and humans, an 0.1 cc dose of the desired dilution is administered intradermally, preferably by injection, once a day.

For one study, 20 dogs were given daily intradermal injections of hypoxanthine. The dose of hypoxanthine was a 0.1 cc dose of a 1:500 dilution of the normal preparation. Therefore, each dose contained 0.00002 mg of hypoxanthine. Of the 20 dogs, all were initially in a condition rated as "poor" by the applicant, an experienced veterinarian. After daily treatment, ranging from two to four weeks, 17 of the 20 dogs were rated in "excellent" condition and the remaining three were evaluated to be in "good" condition. The animal rating of from poor to excellent is analogous to the rating used by Fries in his Human Assessment Questionnaire (HAQ) (see Fries, J. F., et al, Measurement of Patient Outcome in Arthritis, *Arthritis and Rheumatism* 1980; 23:137-145) as follows: excellent—no difficulty; good—some difficulty; fair—much difficulty; and poor—unable to do.

In dogs, intradermal injection of 0.1 cc doses of a 1:500 dilution of the normal preparation has generally proved the most effective; but 0.1 cc doses of dilutions as concentrated as 1:1 (0.01 mg. ($1\times10^{-2}$ mg) active material per dose) or as dilute as 1:500,000 (0.00000002 mg. ($2\times10^{-8}$ mg.) active material per dose) are also expected, in some animals, to be effective.

Studies conducted with LPA on dogs (and horses) and on human arthritic patients have shown that the dog provides a reasonable model for expectations with respect to the effects of hypoxanthine (the ingredient of LPA determined by applicant to be active) administered to humans. As has been mentioned above, extensive experimentation has been conducted with dogs. In 1982, the applicant and 19 other veterinarians administered LPA to 258 dogs and 54 horses. By radiographic examination, 74% of the test animals were diagnosed as being arthritic. The remaining 26% were diagnosed as arthritic without radiographic evidence. An LPA concentrate was diluted 1:500 with sterile saline and the test animals received 0.1 ml of the diluted solution, injected intradermally on a daily basis. It has since been determined that the LPA concentrate used for the experiments contained approximately 300 mg of hypoxanthine per 1,000 ml of LPA concentrate. Therefore, the dose administered to the test animals during the study amounted to approximately 0.00006 mg of hypoxanthine. (It will be recalled that the dose of 0.00002 mg of pure hypoxanthine was administered to the dogs after it was determined that hypoxanthine was the active ingredient in LPA.)

The applicant monitored the administration, response and side effects of the intradermal injection of LPA for four to six months. At the end the treatment, the animals were evaluated on a scale from excellent to poor mentioned above. The excellent through poor ratings were assigned a numerical value of 0-3 respectively, the lower the number implying better condition. On average, the animal patients improved by 1.4 units (i.e. the patient's score decreased by 1.4 units.) Treatment by LPA was compared to other forms of treatment, such as steroids and additional drugs. Of the animals who had been receiving prior treatment, 95% of the dogs and 100% of the horses scored as well or better during the administration of LPA.

It should be noted that the owner's opinion contributed to the evaluation of the animals with respect to whether or not the animals were achieving levels of activity to which they had been previously accustomed. Thus, these study conditions are analogous to those used in human studies that employ commonly accepted "instruments" such as the Stanford HAQ identified in the Fries document mentioned above, which acknowledge and take into account the patient's own attitude about his condition.

Turning now to the human studies, studies were conducted for a minimum of ten months with 90 patients suffering from end stage rheumatoid or osteoarthritis. The Stanford Health Assessment Questionnaire was used to evaluate the quality of life responses to the therapy. Before starting LPA therapy, the patients had exhausted most conventional arthritis treatments, including steroids, gold and non-steroidal antiinflammatory drugs. The human patients received a 0.1 ml of 1:200,000 dilution of LPA stock solution, which was injected intradermally. The dosage was increased uniformly until a clinically measurable response was achieved. Patients normally received two injections per week.

The responses to the questionnaires were statistically evaluated. It was found that 64% of the patients reported improvements in response to LPA therapy over that they had received from conventional therapy. This correlates well with the positive response in the animal studies, which correlation implies that the animal studies with respect to pure hypoxanthine are a good indicator as to the effectiveness of pure hypoxanthine in humans.

Rheumatoid arthritis has proved to be especially sensitive to treatment with hypoxanthine, and improvement in humans is expected from intradermal injection of doses as dilute as 1:10,000 or even 1:500,000 of a normal preparation. In human arthritic patients generally, however, doses of dilutions of about 1:500 are expected to be the most effective. Typically, the desired concentration for a particular human subject would be determined by starting with an initial dose of a 1:20,000 dilution of a normal preparation of hypoxanthine in normal saline, and the concentration of the dose then would be increased by increments (e.g., 1:10,000, 1:1,000, 1:500, 1:100, etc.) until the patient showed improvement, at which time the level would be maintained. In arthritic patients, the dose concentration would be decreased slightly if the subject were to experience increased pain which subsides before the next injection was due. This method of determining the desired effective dose for a particular patient is similar to that used in the treatment of allergies with antigen.

It is apparent that the low doses of hypoxanthine which are the subject of the present invention, may be intradermally administered in a number of ways other than intradermal injection. Two other methods of intradermal administration which would result in the desired delivery of the active material to within the skin, for example to the keratin tissue of the epidermis, are skin patches and trans-dermal carriers.

These and other embodiments will be within the scope of the following claims.

What is claimed is:

1. A method for the treatment of mammalian rheumatoid arthritis and osteoarthritis comprising intradermal administration of at least 95% purity in a dosage range of $2\times10^{-8}$ to $2\times10^{-7}$ grams to a mammal in the need of said treatment.

2. The method of claim 1 wherein said dosage range is of $2\times10^{-7}$ to $2\times10^{-6}$ grams.

3. The method of claim 1 wherein said dosages range is of $2\times10^{-6}$ to $1\times10^{-5}$ grams.

* * * * *

UNITED STATES PATENT AND TRADEMARK OFFICE
CERTIFICATE OF CORRECTION

PATENT NO. : 4,931,431

DATED : June 5, 1990

INVENTOR(S) : William S. Livingston

It is certified that error appears in the above—identified patent and that said Letters Patent is hereby corrected as shown below:

Column 2, lines 28-29, after "intradermally", insert --.--

Column 4, line 53, after "administration", insert --of hypoxanthine--

On the title page:
In the Abstract, line 7, change "does" to --dose--

Signed and Sealed this

Eighteenth Day of February, 1992

Attest:

HARRY F. MANBECK, JR.

Attesting Officer

Commissioner of Patents and Trademarks